US010071264B2

(12) United States Patent
Liger

(10) Patent No.: US 10,071,264 B2
(45) Date of Patent: Sep. 11, 2018

(54) IRRADIATION DEVICE USING IONIZING RADIATION, PARTICULARLY FOR RADIOTHERAPY AND/OR RADIOBIOLOGY

(71) Applicant: P M B, Peynier (FR)

(72) Inventor: Philippe Liger, Peynier (FR)

(73) Assignee: P M B, Peynier (FR)

( * ) Notice: Subject to any disclaimer, the term of this patent is extended or adjusted under 35 U.S.C. 154(b) by 162 days.

(21) Appl. No.: 15/035,282

(22) PCT Filed: Nov. 20, 2014

(86) PCT No.: PCT/FR2014/052979
§ 371 (c)(1),
(2) Date: May 9, 2016

(87) PCT Pub. No.: WO2015/075388
PCT Pub. Date: May 28, 2015

(65) Prior Publication Data
US 2016/0287905 A1 Oct. 6, 2016

(30) Foreign Application Priority Data
Nov. 20, 2013 (FR) ..................................... 13 02672

(51) Int. Cl.
*A61N 5/10* (2006.01)

(52) U.S. Cl.
CPC ......... *A61N 5/1067* (2013.01); *A61N 5/1071* (2013.01); *A61N 2005/1074* (2013.01); *A61N 2005/1089* (2013.01)

(58) Field of Classification Search
CPC ................ A61N 5/1067; A61N 5/1071; A61N 2005/1089; A51N 2005/1074

(Continued)

(56) References Cited

U.S. PATENT DOCUMENTS 6,445,766 B1 9/2002 Whitham
7,567,647 B1 7/2009 Maltz
(Continued)

FOREIGN PATENT DOCUMENTS

WO 2007/017177 A1 2/2007
WO 2012/085507 A2 6/2012

OTHER PUBLICATIONS

Hafiz M Zin et al: "Towards real-time VMAT verification using a prototype, high-speed CMOS active pixel sensor", Physics in Medicine and Biology, Institute of Physics Publishing, Bristol GB, vol. 58, No. 10, Apr. 25, 2013 (Apr. 25, 2013), pp. 3359-3375, XP0202447700, ISSN: 0031-9155, DOI: 101088/0031-9155/58/10/3359, the whole document.

(Continued)

*Primary Examiner* — Nicole Ippolito
(74) *Attorney, Agent, or Firm* — Young & Thompson; Eric Jensen; Roland Long

(57) ABSTRACT

An irradiation device using ionizing radiation, particularly for radiation therapy and/or radiation biology, simultaneously includes: at least one unit (MER) for emitting ionizing radiation; at least one dose-monitoring unit (MCD); at least one unit for detecting an ionizing radiation dose (MDD); and at least one monitoring and control system (SCC). The units (MER, MDD, MCD) and the system (SCC) are also intelligently interconnected therebetween so as to engage with one another and form an intelligent monitoring and adjustment loop, such as to controllably, precisely and desirably produce strong doses of ionizing radiation of at least 0.01 Gy, having a precision within at least one 1μ Gy but preferably 1 n Gy, in strong dose rates up to 1000 Gy/s with power within a range of 1 to 50 Me V in very brief time intervals of at least 0.1 μs, preferably 1 ms.

14 Claims, 4 Drawing Sheets

Figure 1:
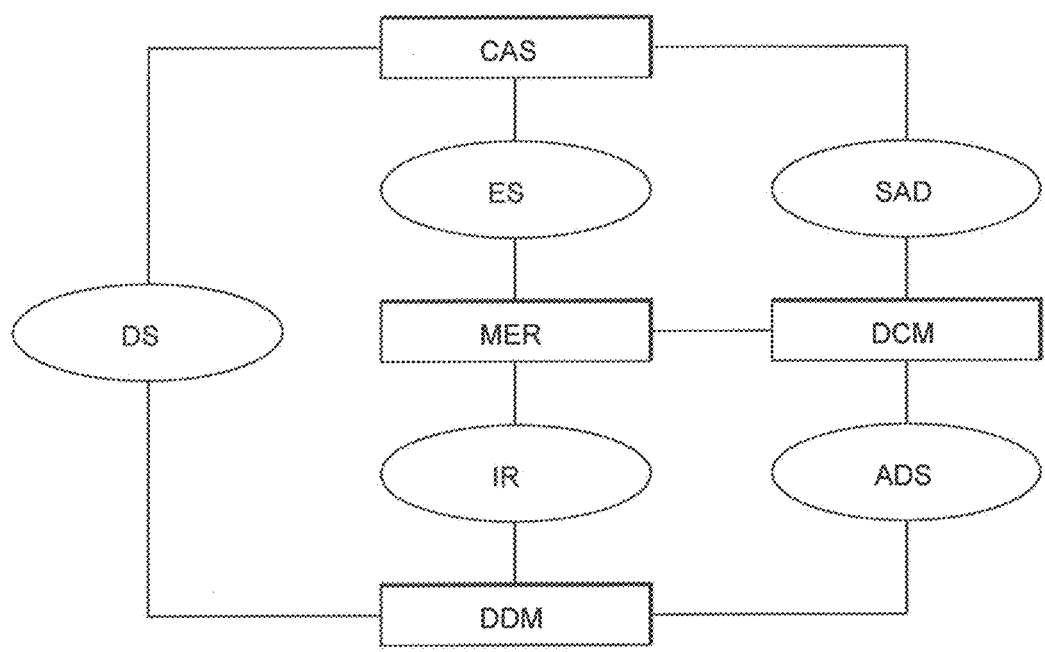

(58) Field of Classification Search
USPC .............................. 250/492.1, 492.3; 600/1
See application file for complete search history.

(56) References Cited

U.S. PATENT DOCUMENTS

| | | | |
|---|---|---|---|
| 7,807,987 B2* | 10/2010 | Braess | A61N 5/1048 250/491.1 |
| 8,389,957 B2* | 3/2013 | Jaffe | G01N 21/6408 250/216 |
| 2008/0144772 A1 | 6/2008 | Yi et al. | |
| 2011/0178359 A1* | 7/2011 | Hirschman | G21F 5/015 600/4 |

OTHER PUBLICATIONS

Li Ji et al: "Improvements in dose accuracy delivered with static-MLC IMRT on an integrated linear accelerator control system", Medical Physics, AIP, Melville, NY, US, vol. 39, No. 5, May 1, 2012 (May 1, 2012), p. 2456-2462, XP012161002, ISSN: 0094-2405, DOI: 10.1118/1.3701778 [retrieved on Apr. 13, 2012], whole document.

International Search Report, dated Mar. 12, 2015, from corresponding PCT Application.

* cited by examiner

IRRADIATION DEVICE USING IONIZING RADIATION, PARTICULARLY FOR RADIOTHERAPY AND/OR RADIOBIOLOGY

The present invention concerns an irradiation device using ionizing radiation, particularly for radiotherapy and/or radiology capable of programmed delivery, in controlled and accurate manner, of high doses of ionizing radiation of at least 0.25 Gy, preferably 10 Gy, with an accuracy of at least 1 µGy, preferably 1 nGy, in an energy range comprised between 1 MeV and 50 MeV, in very short times, that is to say for example of at least 0.1 µs, preferably 100 µs, or even 1 ms, or for instance 100 ms.

It also concerns an irradiation device using ionizing radiation provided with a power pulse control system capable of producing a beam of energy particles that is adjustable in a range comprised between 1 MeV and 50 MeV, pulsed at a desired frequency (f) with an adjustable pulse duration (d) of at least 1 ns, preferably 0.1 µs, and capable of delivering an absorbed dose rate of up to 250 Gy/s or even of up to 500 Gy/s or even up to 1000 Gy/s.

It more particularly concerns an irradiation device using ionizing radiation particularly for radiotherapy and/or radiobiology wherein the various means and systems constituting it are interconnected with each other intelligently to cooperate and form a loop for control and regulation, in particular of the power, so as to provide controlled and accurate delivery of high doses of ionizing radiation of at least 0.25 Gy with an accuracy of at least 1 µGy, preferably 1 nGy, at energies in a range comprised between 1 MeV and 50 MeV, for very short times, that is to say for example of at least 0.1 µs, preferably 100 µs, or even 1 ms, or for instance 100 ms.

It possibly concerns an irradiation device using ionizing radiation particularly for radiotherapy and/or radiobiology comprising a fast detector, also qualified as "ultra-fast", capable of detecting a dose in very short times, for example in at least 0.01 ns, coupled to control electronics capable of controlling a delivered dose for a fraction of a second, for example for at least 0.1 µs, preferably 1 µs or 1 ms, and preferably for less than one second, or even less than 200 ms.

Radiotherapy is a method of loco-regional treatment of cancers. It is, with surgery, the most frequent treatment for cancers and may lead to clear remission by itself. It may be used alone or associated with surgery and chemotherapy. Its indications are linked to the type of tumor, to its location, its stage and to the general state of the target. In certain cases, it presents the advantage of being carried out on an outpatient basis on account of the fact that the sessions may be of short duration and the secondary effects less than those of a chemotherapy. For this, the radiotherapy uses radiations to destroy the cancer cells by affecting their capacity to reproduce. The irradiation is directed to destroying all the tumor cells while sparing healthy peripheral tissues.

Generally, an irradiation device using ionizing radiation for radiotherapy and/or radiobiology comprises an ion or electron beam linear accelerator and control and actuation electronics which enables the emission of ionizing radiation to be generally stopped when the dose specified by the operator has been attained.

At the present day, conventional radiotherapy machines enable ionizing radiation to be delivered in the form of electrons or X-rays at energies of 3 to 25 MeV, at doses of the order of 1 Gy, with a dose rate of the order of 4 Gy per minute and with mediocre accuracy.

Solutions have been proposed to obtain an accuracy for the radiation doses delivered of the order of 1%. More particularly, as of now, the irradiation times, the doses delivered and the collimations are programmed by an operator who is a medical physicist in cooperation with a radiotherapist using information technology tools. Unfortunately, this accuracy cannot be attained with conventional devices for detecting and controlling the dose and/or the rate of dose delivered and/or absorbed. To be precise, the major problems of these devices are characterized by the fact that they are not capable of controlled and accurate delivery, in programmed and intelligent manner, of high doses of ionizing radiation of up to 250 Gy/s, or up to 500 Gy/s or even up to 1000 Gy/s, at energies in a range comprised between 1 MeV and 50 MeV, in very short times, that is to say for example of at least 0.1 µs, preferably 100 µs, or even 1 ms, or for instance 100 ms.

Another major technical problem of these devices is that the various members composing said devices are not sufficiently fast and/or interconnected with each other in an intelligent manner to cooperate together and form a sufficiently fast loop for regulation and control of the dose and/or of the dose rate sufficiently high to deliver a dose of ionizing radiation with accuracy in very short times.

Particularly, another major technical problem of these devices is that the detector used is not fast, which renders impossible the detection of the dose at very short timescales, for example of the order of the nanosecond.

Particularly, another major technical problem of these devices is that the detector used saturates above a certain dose rate, generally as of 10 Gy/s at best, which renders impossible the detection of very high dose rates, for example of the order of 250 Gy/s, or even 500 Gy/s or for instance 1000 Gy/s.

Another technical problem which arises is that the dose control means and the control and actuation means are not effective for executing in desired manner and in a very accurate way, the delivery of a specified dose in a very short time.

To obtain good accuracy in the dose delivered in the course of an irradiation of a duration of a few milliseconds or of the order of the second, it suffices for the times that separate the start of the detection by the control and actuation electronics from the start of the emission by the accelerator, and that separate the moment of the detection by the control and actuation electronics of the exceeding of the specified dose from the stopping of the emission by the accelerator, to be less than one millisecond, preferably less than a few microseconds.

The technical problems previously raised lead to an incapacity to deliver and/or to measure and/or to accurately control high doses of ionizing radiation in very short times. The impacts of poor control of dose and/or of the dose rate absorbed by the target may lead purely and simply to the destruction of the healthy cells, tissues or organs and the secondary effects which ensue therefrom may in certain cases, have detrimental effects on the organs at risk.

From the state of the art, irradiation devices using ionizing radiation are known which are capable of delivering dose rates as high as 10 kGy/s but with electrons only and at energies less than or equal to 10 MeV.

Accelerators are also known from the state of the art comprising control systems for inhibiting an irradiation in less than 100 µs, but their ionizing chamber detection system is not sufficiently fast to detect the dose rate, integrate it, compare it and stop the irradiation in less than 100 ms.

Today, it would appear imperative to design an architecture for an irradiation device using ionizing radiation, particularly for radiotherapy and/or radiobiology, enabling controlled and accurate delivery of high doses of ionizing radiation of at least 0.25 Gy, with an accuracy of at least 1 μGy, preferably 1 nGy, in very short times, that is to say at least 0.1 μs, in particular 100 μs, or even 1 ms, or even 100 ms, in energy ranges comprised between 1 MeV and 50 MeV.

From the publication WO 2007 017177 there is known a radiotherapy device comprising a pulsed source of electrons, capable of providing a total exposure over at least one minute at the repetition frequency of 1 Hz and of providing single doses of 10 Gy in approximately 30 ns.

From the publication US 2010 329413 there is known a radiotherapy device comprising a system and a method capable of delivering X-rays with a dose rate capable of attaining approximately 10 Gy/s (gray per second), or even appreciably more.

From the publication U.S. Pat. No. 6,445,766 there is also known a radiotherapy device comprising means for producing an ionizing radiation.

From the publication U.S. Pat. No. 7,567,647 and US 2008 144772 there is known a radiotherapy device comprising a means for emitting ionizing radiation, a target, a dose detector, and a dose control means.

However, none of the cited documents discloses a specific regulation and control loop intelligently linking the various members composing the device for emitting ionizing radiation to deliver in effective manner a dose of at least 1 Gy, in particular of at least 10 Gy in energy ranges comprised between 1 MeV and 25 MeV and preferably up to 50 MeV, in very short times, that is to say of at least 0.1 μs, preferably 100 μs, or 1 ms, or even 100 ms.

Furthermore, none of the cited documents discloses a detector capable of detecting a dose in very short times, preferably of at least 0.01 ns, that is to say an ultra-fast detector.

Moreover, none of the cited documents meets all the specifications for delivering a dose rate of ionizing radiation up to 250 Gy/s, or even up to 500 Gy/s or even up to 1000 Gy/s, in an energy range comprised between 1 MeV and 25 MeV, or even 50 MeV, in a way that is controlled during times less than 1 s, in particular 1 ms.

The object of the present invention is to provide an irradiation device using ionizing radiation in particular for radiotherapy and/or radiobiology mitigating the problems referred to earlier and improving the known irradiation devices using ionizing radiation of the state of the art.

In the following description, the terms listed below will have the following definition:

Absorbed dose: the absorbed dose, or more concisely dose of ionizing radiation or the dose, is the energy imparted per unit mass of material subjected to the ionizing radiation. The absorbed dose measures the density of energy per unit mass imparted by irradiation. The unit of dose in the SI system is the gray (Gy); it is a derived unit with the value of one joule per kilogram: 1 Gy=1 J/kg. Considering a beam of ionizing radiation irradiating an element of volume dV, volumetric mass density ρ and mass dm=ρdV. Let dE be the energy imparted in that element by the beam, the absorbed dose D is defined by:

$$D = \frac{dE}{dm} = \frac{1}{\rho}\frac{dE}{dV}$$

Absorbed dose rate: absorbed dose by the material subjected to ionizing radiation, per unit time. It is measured in Gy/s (grays per second) in the SI system.

Electronvolt: of which the symbol is eV, is a unit of energy measurement. Its value is defined as being the energy acquired by an electron accelerated by a potential difference of one volt: 1 eV=e·(1 V), where e is the absolute value of the charge of the electron.

Mega-electron-volt: of which the symbol is MeV, 1 MeV=$10^6$ eV=$1.6022 \times 10^{-13}$ J.

Nanosecond: Unit of time measurement of the SI system, of value $10^{-9}$ second, and of which the symbol is ns.

Microsecond: Unit of time measurement of the SI system, of value $10^{-6}$ second, and of which the symbol is μs.

Millisecond: Unit of time measurement of the SI system, of value $10^{-3}$ second, and of which the symbol is ms.

Second: Unit of time measurement of the SI system of which the symbol is s.

Very accurate detection: measurement of a quantity of which the relative uncertainty of the result is very small, of at most 0.01%.

Ionizing radiation: radiation capable of imparting enough energy to the material it passes through to create ionization, that is to say to ionize atoms and/or molecules which constitute said material.

High dose: dose of ionizing radiation which, according to the type of ionizing radiation, produces deterministic effects on a living organism or else is greater than that which a target can receive during the course of its life by the natural ionizing radiations and those due to human activity. Whatever the type of ionizing radiation, a high dose is characterized by an absorbed dose greater than 0.01 Gy.

Intelligent interconnection: this is an interconnection which uses information technologies so as to optimize the transfer and the distribution of information, and which is directed to optimizing the entire mesh of an electrical network in order to improve the efficiency of transfer and the response to a given actuation.

A desired value: generally, this is a chosen value, defined and programmed by an operator via the man-machine interface.

Intelligent control: this is a control which uses information technologies so as to optimize the value of a quantity to control, the transfer and the distribution of information, and which is directed to optimizing the control of entire mesh of an electrical network in order to improve the efficiency of transfer and the response to a given actuation.

The invention is directed to an irradiation device using ionizing radiation, in particular for radiotherapy and/or radiobiology, simultaneously comprising at least:

a means for emitting ionizing radiation (MER) comprising:

at least one particle source which comprises at least:

a cathode and an anode, or a plasma, a means for triggering particle emission, in particular a grid or an electrode or a laser and a means for accelerating a particle beam, said means for emitting ionizing radiation (MER) also being provided with a power pulse control system which is configured for producing a particle beam, that is to say ionizing radiation, of energy, adjustable and desired, in a range comprised between 1 MeV and 50 MeV, pulsed at a desired frequency (f), typically comprised between 5 Hz and 1000 Hz, or even between 5 Hz and 500 Hz, or even between 5

Hz and 200 Hz, and preferably approximately 100 Hz, with a pulse duration (d), which is adjustable, of at least 1 ns, and preferably comprised between 0.05 µs and 12 µs, and which is preferably 0.1 µs, and for delivering an absorbed dose rate of at least approximately 0.01 Gy/s, for example comprised between approximately 0.01 Gy/s and approximately 250 Gy/s, or even 500 Gy/s or even 1000 Gy/s, an ionizing radiation dose detection means (DDM) comprising a detector; the detector being an ultra-fast detector, coupled to a dose control means (DCM), configured to detect, very accurately, a dose of ionizing radiation in very short times, that is to say in at least 0.01 ns, and at very high dose rates that is to say making it possible to deliver at least 0.01 Gy/s, for example 25 Gy/s or even 50 Gy/s, or even preferably 250 Gy/s, or even 500 Gy/s or even 1000 Gy/s, the dose control means (DCM), configured to control triggering and stopping of the means for emitting ionizing radiation (MER), comprising:

control electronics (CE), configured for controlling a dose delivered for a fraction of a second, that is to say for at least 0.1 µs, or even 100 µs, or even 1 ms, or even 100 ms.

an amplifier and/or an attenuator amplifying and/or attenuating a signal emitted by the detector, an integrator integrating, during the time of the emission, said amplified and/or attenuated signal and a comparator continuously comparing said integrated signal to the settings for the specified dose (SAD) predetermined by an operator, a control and actuating system (CAS), comprising:

a system for functional control (SFC) of the various members of said device, comprising:

a man-machine interface (MMI), viewing tools and implementation means configured in order for an operator to program, in a controlled, desired and very accurate manner, at a single time, the nature of the radiation, the absorbed dose rate of ionizing radiation, a duration and pulse settings for the emission of the ionizing radiation.

said means (MER, DDM, DCM) and said system (CAS), constituting at least in part said device and being furthermore connected together intelligently to cooperate and form an intelligent loop for control and regulation, in particular of the power, are configured to deliver and control doses of ionizing radiation of at least 0.01 Gy or even 0.25 Gy with an accuracy of at least 1 µGy, preferably 1 nGy, at energies comprised between 1 MeV and 50 MeV, for very short times, that is to say at least 0.1 µs, or even 100 µs, preferably 1 ms, or even 100 ms, or for example comprised between 0.1 µs and 100 ms, preferably 100 µs or 1 ms.

According to other features of the invention, the means for emitting ionizing radiation (MER) is a particle accelerator which comprises a power source and control electronics, that is to say a pulse control system, said control electronics (or pulse control system) is directly linked to the dose control means (DCM) so as to automatically stop the power source when the absorbed dose, detected and measured, has attained a value specified and predetermined by the operator via the man-machine interface (MMI), said man-machine interface (MMI) further comprises a command station (CS) and a viewing interface management program.

According to other features of the invention, the acceleration means either uses microwave frequency waves, or is induction-based, or is electrostatic-based.

Advantageously, the means for emitting radiation (MER) further comprises several acceleration means mounted in series and/or interleaved with means for deviation or recirculation of the particle beam through the said one or more acceleration means, each being supplied by at least one power source.

Advantageously, the detector is a semiconductor, in particular diamond, for example in monocrystalline or polycrystalline form, pure or doped, or silicon carbide, comprised between two polarization electrodes at the terminals of which is applied a potential of several volts adjustable according to the thickness of the detector via the man-machine interface, and is configured to obtain a very short response time, for example of at least 0.01 ns, at high dose rates, that is to say of at least 0.01 Gy/s.

Conventionally, the semiconductor-based detectors were used for much lower energy ranges than in the context of the present invention, typically less than 1 MeV and are known for having as drawbacks the fact of having variable sensitivity, making them particularly poorly adapted to the medical field.

However, in the context of the present invention, the detector is passed through by the beam and is configured to enable monitoring of the dose delivered to the patient during the treatment. It thus detects the entirety of the ionizing radiation stream in real time. It could thus have been expected for the known detectors to provide information difficult to interpret, on the one hand, and especially for them to saturate in the range of doses considered, but it has become surprisingly apparent that, contrary to the prejudice of the person skilled in the art, detectors of this type, while being passed through by the entirety of the ionizing radiation stream adapted to be applied to a patient, enabled a significant value of that stream to be given, both precisely and rapidly.

A diamond detector that is promising in the context of the present invention is for example developed by the LCD laboratory (LCD standing for Laboratoire Capteur Diamant) of the CEA in Saclay.

For a detector of silicon carbide, one of those studied and developed by the IM2NP laboratory (IM2NP standing for Institut Matériaux Microélectronique Nanosciences De Provence—which may be translated as Materials Microelectronics Nanosciences Institute of Provence—, UMR CNRS 7334), which is specialized in silicon carbide, provides the first interesting initial results.

Advantageously, the control electronics (CE) of the dose control means (DCM) comprises means for measuring electric current, in particular of an electrical signal, produced by the interaction of the radiation with the detector, means for converting said electric current into absorbed dose rate units and means for integrating said electric current that are configured to accurately measure the absorbed dose accumulated during the emission of the ionizing radiation.

Advantageously, an electrical signal is produced by the detector, said electrical signal is measured and integrated by an electrometer during the emission of the radiation, the integrated value of said electrical signal is directly compared to the value of the dose specified and predetermined by the operator via the man-machine interface such that, as soon as the integrated value is greater than or equal to the specified and predetermined value, the signal of the system for triggering particle emission is interrupted to instantaneously stop, prevent, the emission of the radiation and, possibly, preferably the high voltage source in a sufficiently short time, for example of at least 1 ns.

According to other features of the invention, the detector comprises one or more quadrants or sectors or voxels each producing a detection signal or absorbed dose signal (ADS) and which are intelligently disposed, that is to say configured to enable information to be deduced, from their detection signals (ADS), characterizing the position, the shape and/or the energy of the ionizing radiation beam which passes through them, and furthermore so as to control and regulate the ionizing radiation beam, in particular its position, its shape and/or its energy.

Figure 2:
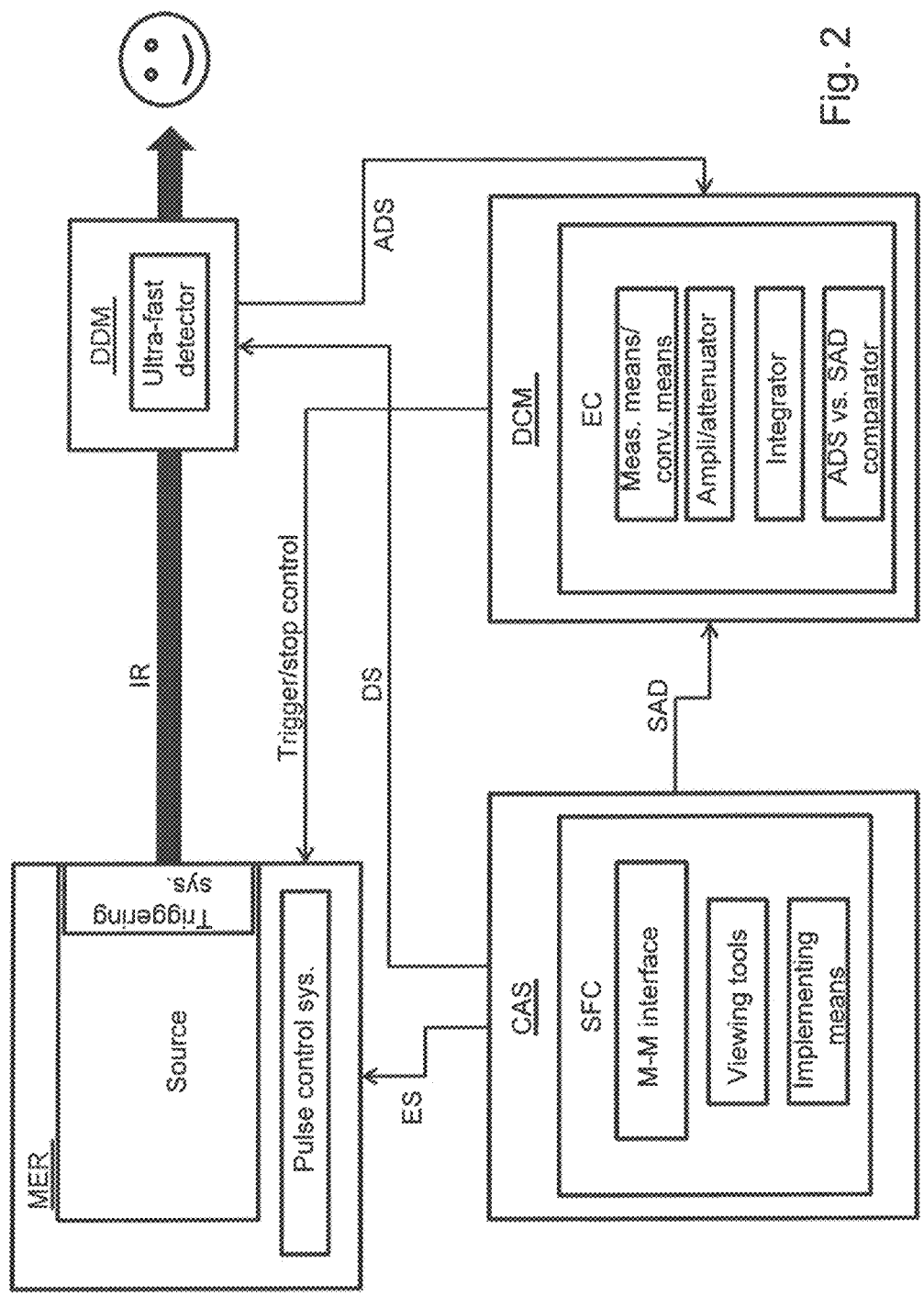
Figure 3:
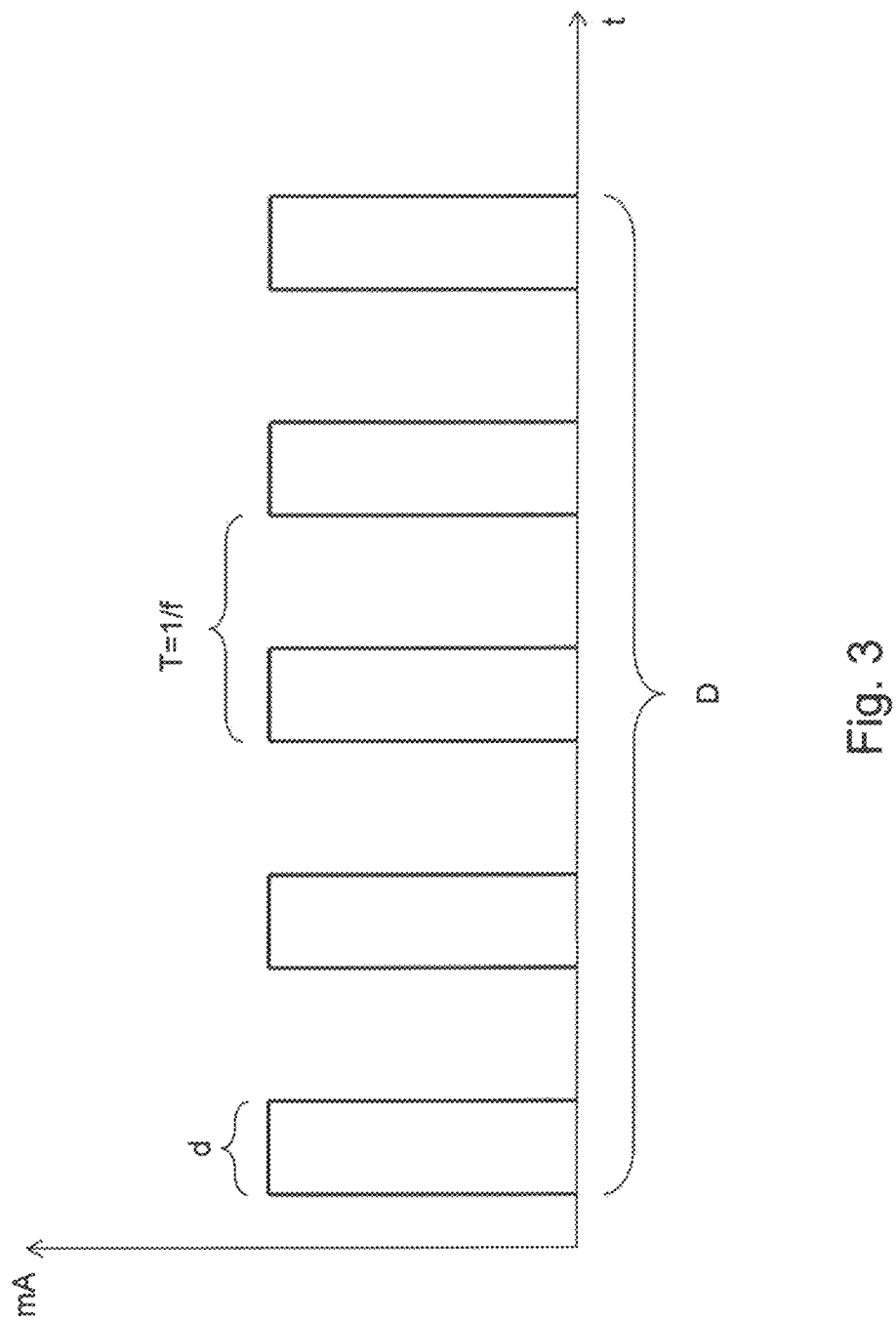
Figure 4:
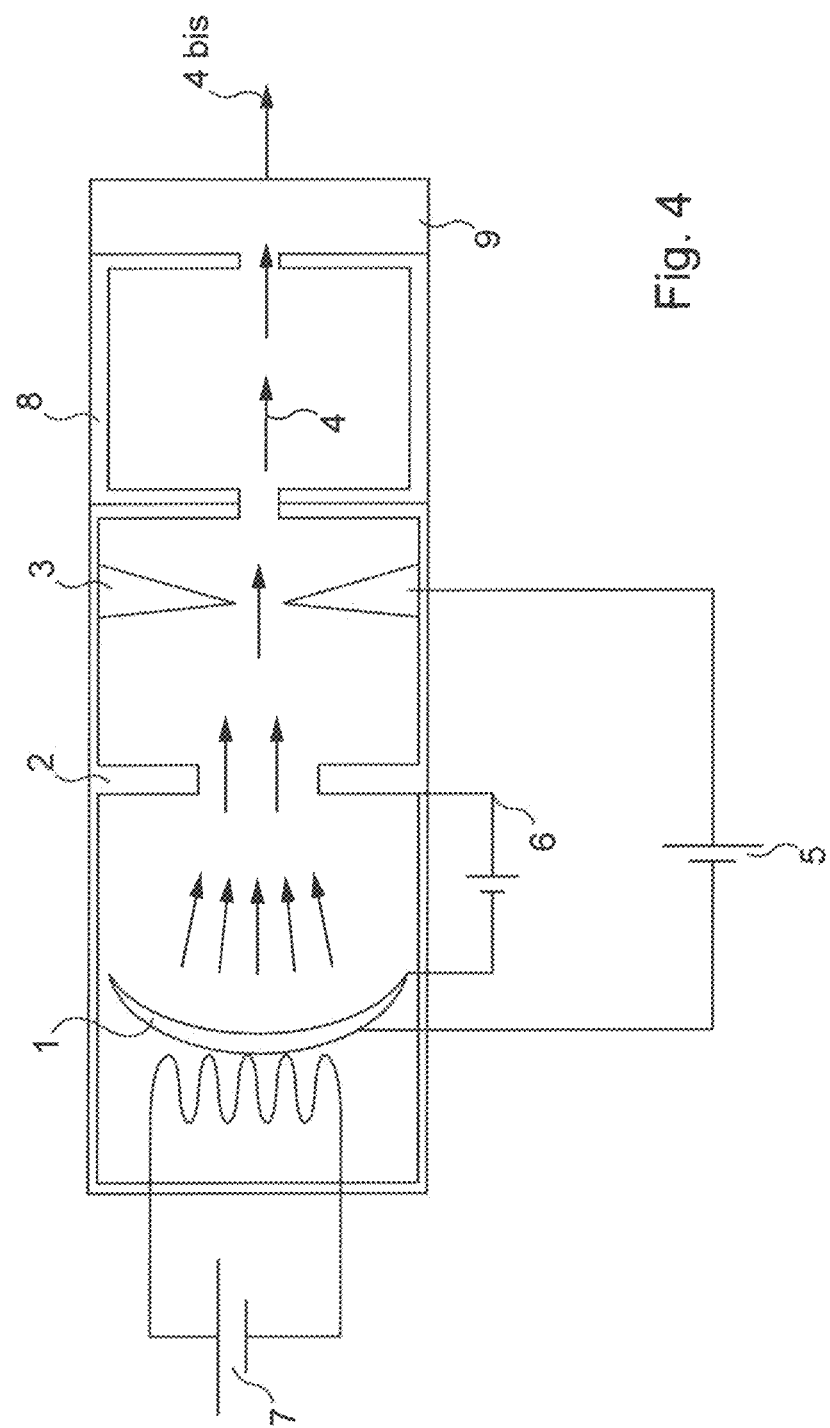

Other features and advantages of the invention taken alone or in combination, will appear on reading the following detailed description for the understanding of which reference will be made to the accompanying drawings in which:

FIG. 1 is a diagrammatic representation of a general operating principle of the various means and members of the device according to the invention defining a regulation and control loop, FIG. 2 is a diagrammatic presentation of an embodiment of a device according to the invention, FIG. 3 illustrates some of the main parameters for a dose, i.e. the firing the duration (D), the duration of a pulse (d) and the pulse frequency (f), and FIG. 4 is a diagrammatic representation of an example means for emitting ionizing radiation (MER).

FIG. 1 shows a general description of the principle of intelligent interconnection of the various members composing the irradiation device using ionizing radiation for radiotherapy and/or radiobiology of the present invention. This principle shows that the various members and/or sub-members constituting the device according to the invention cooperate together and form a control and regulation loop, in particular for control and regulation of power so as to provide controlled and accurate delivery of high doses of ionizing radiation of at least 0.25 Gy with an accuracy of at least 1 µGy, preferably 1 nanogray (nGy), in an energy range comprised between 1 MeV and 50 MeV, in very short times, that is to say for example comprised between 0.1 µs and 100 ms, preferably 100 µs or 1 ms. This cooperation and interconnection and the loop formed are essential to obtain the technical functions of the present invention. The association of the technical settings, in particular electronic, at each level of the control and regulation loop shows the many reasons why this interconnection is necessary to produce the invention and enables the operation of the device and the delivered dose to be controlled accurately and without ambiguity.

With reference to FIGS. 1 and 2, the device comprises four members connected together: at least one means for emitting ionizing radiation (MER), a means for detecting the dose (DDM), a control and actuating system (CAS) and a dose control means (DCM).

The control and actuating system (CAS) is programmed by an operator via a software interface so as to send, in real time, signals of emission settings (ES) to the means for emitting ionizing radiation (MER), signals for detection settings (DS) to the means for ionizing radiation dose detection (DDM) and signals for absorbed dose settings (SAD) to the ionizing radiation dose control means (DCM).

Also, the means for emitting ionizing radiation (MER) emits ionizing radiation (IR) corresponding to the ionizing radiation signal which interacts with the dose detection means (DDM).

The interaction of the ionizing radiation (IR) with the dose detection means (DDM) generates the sending of an absorbed dose signal (ADS), by the dose detection means (DDM) to the dose control means (DCM). Said dose control means (DCM) amplifies or attenuates, integrates and compares the absorbed dose signal (ADS) with the signal for absorbed dose setting (SAD). If the result of the amplification or of the attenuation and of the integration of the absorbed dose signal (ADS) is greater than or equal to the signal for absorbed dose setting (SAD), the absorbed dose control means (DCM) sends a signal which actuates the interruption of the means for emitting ionizing radiation (MER), otherwise the emission of ionizing radiation (IR) continues according to the specifications predefined by the operator.

The arrangement of the various members for setting, control and their interconnections constituting the control and regulation loop makes it such that it is possible to provide controlled and accurate delivery, in intelligent manner, of high doses of ionizing radiation of at least 0.25 Gy with an accuracy of at least 1 µGy, preferably 1 nGy, in an energy range comprised between 1 MeV and 50 MeV, during very short times, that is to say for example comprised between approximately 0.1 µs and 100 µs, preferably 100 µs or 1 ms.

The dose detection means (DDM) comprises in particular the ultra-fast detector capable of detecting, very accurately, a dose in very short times, for example of at least 0.01 ns, coupled to a dose control means (DCM), which comprises control electronics (CE). Said control electronics (CE) is capable of controlling a delivered dose of at least 0.01 Gy, or at least 0.25 Gy for at least 0.1 µs, or even 100 µs, or even 1 ms, or even 100 ms.

The ultra-fast detector of the dose detection means (DDM) is in particular of diamond and is comprised between two polarization electrodes at the terminals of which is connected the control electronics (CE) of the dose control means (DCM), which measures the detection electrical signal (ADS), in particular the current, produced by the ionizing radiation through the diamond, converts it into absorbed dose rate monitoring units and integrates it to give a measurement of absorbed dose accumulated during the radiation emission. The electronics for converting the electrical signal produced by the interaction of the diamond and the ionizing radiation is for example calibrated using an instrument for absolute measurement of absorbed dose accumulated during an emission of ionizing radiation.

According to other features of the invention which are particularly advantageous, the ultra-fast detector comprises one or more of what are referred to as "primary" detectors which each comprise several small detectors qualified as secondary, that is to say one or more quadrants or sectors or voxels each producing a detection signal (ADS) and which are disposed so as to deduce information, from their detection signals (ADS), characterizing the position, the shape and/or the energy of the ionizing radiation beam which passes through them, and furthermore so as to control and regulate the ionizing radiation beam, in particular its position, its shape and/or its energy. For example, it comprises four quadrants or sectors or voxels disposed in a square.

For example, each detector qualified as primary detector comprises several detection zones or several small detectors qualified as secondary. The ultra-fast detector may be a stack of primary detectors in the form of discs of semiconductor material, separated into several secondary detectors.

Advantageously, detector is a semiconductor, in particular diamond, comprised between two polarization electrodes at the terminals of which is applied a potential of several volts adjustable via the man-machine interface, which makes it possible to obtain a very short response time, for example of at least 0.01 ns, at high dose rates, that is to say of at least 0.01 Gy/s. According to another advantageous example embodiment, said detector may be produced from silicon carbide. The semiconductor, in particular the diamond, is included between two polarization electrodes at the terminals of which is applied a polarization potential of a few volts (PP) for example one volt per micron of diamond thickness between the electrodes.

As described above, the polarization voltage (PP) is adjustable by the control and actuation system (CAS) via the man-machine interface. At the terminals of the polarization electrodes is connected a means for polarization interconnection which makes it possible both to provide the polarization potential (PP) actuated by the control and actuation system (CAS) and to send the absorbed dose signal (ADS) produced by the diamond by interaction with the ionizing radiation by dose control means (DCM).

Advantageously, the dose control means (DCM) comprises means for measuring the electrical signal (ADS), in particular for measuring current, produced by the radiation emitted through the detector, in particular by interaction between the detector and the ionizing radiation which passes through it, means for converting said detection electrical signal (ADS), in particular for current, into absorbed dose rate monitoring units and means for integrating said detection electrical signal (ADS), in particular for current, so as to accurately measure the absorbed dose accumulated during the emission of the ionizing radiation.

The chosen detector provides the advantage of having a very short response time of the order of the nanosecond or even of an order less than the nanosecond. It also provides high resistance to the ionizing radiation, interaction properties with the ionizing radiation similar to those of water, that is to say that the energy imparted by the ionizing radiation in passing through it is comparable to that which the same radiation would impart in water, the conversion of such energy into detection electrical signal (ADS) making the latter representative of the dose imparted by the ionizing radiation in living matter, typically a patient. It also provides a linear response in terms of current of the electrical signal relative to the dose rate over wide intervals of high dose rates, and/or to the pulse duration (d) of the ionizing radiation. It also provides a constant response in terms of current relative to the energy of the ionizing radiation.

These various physical and possibly chemical properties make diamond in particular an appropriate material for measuring high dose rates of ionizing radiation, in particular dose rates of at least 25 Gy/s or even at least 50 Gy/s, in very short pulses of ionizing radiation of the order of 100 ns, for a long lifetime, that is to say at least 500 hours.

The control and actuation system (CAS) is provided with a functional control system of the various members of said device according to the invention. This control and actuation system (CAS) mainly comprises the man-machine interface (MMI) comprising several buttons and members for management and programming of the device, in particular with regard to dose or absorbed dose rate or delivered dose rate of ionizing radiation. The control and actuation system (CAS) further comprises viewing tools and serial secondary control means, in particular tactile and non-tactile means, switches, etc., necessary for the implementation of the device. These means enable an operator to perform controlled, desired and very precise programming, in intelligent manner, at a single time, of the nature of the radiation, of the absorbed dose and/or of the absorbed dose rate and possibly of the delivered dose rate, of ionizing radiation, in a desired time, and the pulse settings.

The pulse parameters of grid, amplitude, pulse frequency (f) and duration (d), number of pulses per pulse train or pulse train duration, time between pulse trains and the number of pulse trains or total emission duration (D) (as shown diagrammatically in FIG. 3) are defined by the operator via the man-machine interface and adapted software. These parameters are sent to electronics programmed to generate synchronization signals for the high frequency (HF) pulses of the accelerator and electron cannon grid pulses or particle beam source triggering. The signals are amplified by low voltage electronics to produce grid pulses and by power electronics for the production of high frequency (HF) pulses.

Furthermore, the detector, as described above, is placed in the beam of ionizing radiation to measure the absorbed dose rate which that ionizing radiation is able to produce in the material with which it interacts, typically a patient. The signal (ADS) produced by the detector in the form of an electric current is measured and integrated by the control electronics (CE) of the dose control means (DCM), in particular an electrometer, during the emission of the ionizing radiation and the integrated value is compared to the value of the absorbed dose (SAD) specified by the operator via the man-machine interface (MMI). As soon as the integrated value is greater than or equal to the specified value, the grid pulse signal falls to its polarization potential that is negative relative to the cathode so as to prevent the emission. The ionizing radiation emission duration can thus be controlled and stopped in real time and the delivered dose is accurate to the nearest dose produced by the last ionizing radiation pulse.

The detection signal measurement function may for example be provided by an amplifier or an attenuator according to the amplitude of the signal, followed by a sample-and-hold device. The dose control means (DCM) is a means configured to control the triggering and the stopping of the means for emitting ionizing radiation (MER), and it comprises the control and actuation electronics (CE). In a particularly convenient example embodiment, the control and actuation electronics (CE) comprises the amplifier or attenuator amplifying or attenuating, according to the amplitude, a signal emitted by the detector, the integrator integrating during the emission duration of said amplified or attenuated signal and the comparator continuously comparing said integrated signal to the settings for specified dose (SAD) predetermined by the operator.

To actuate the emission of ionizing radiation for very short times, the emitter (MER) is constituted by a power source which is triggered and stopped by the electronics of the control and actuation system (CAS). The operator actuates the triggering of an emission programmed via the man-machine interface (MMI). The electronics of the control and actuation system (CAS) coupled to the dose control means (DCM) stops the power sources when the absorbed dose, detected and measured, attains the value specified and predetermined by the operator.

Thanks to fast electronics of the dose control means (DCM), when the amplified or attenuated and integrated signal from the detector (ADS) equalizes the setting signal for the dose (SAD), the signal output from the comparator automatically falls to a predetermined and predefined value and triggers the stopping of the electron beam source, in particular the means for emitting ionizing radiation (MER), and the stopping of the high voltage source (HV) of the accelerator in a sufficiently short time, that is to say preferably less than 100 μs such that the detected dose does not exceed the specified dose.

All the above-cited means constituting the loop for control and regulation, in particular of power, constituting the device of the present invention, are interconnected with each other intelligently as described above, to cooperate and form an intelligent loop for control and regulation, in particular of power, so as to provide controlled and accurate delivery of high doses of ionizing radiation, that is to say preferably of at least 0.01 Gy and preferably of at least 0.25 Gy with an accuracy of at least 1 µGy, preferably 1 nGy, in an energy range comprised between 1 MeV and 50 MeV, during very short times, that is to say for example comprised between approximately 0.1 µs and 100 ms, preferably 100 µs or 1 ms.

Advantageously, the means for emitting ionizing radiation (MER) is constituted principally by the particle accelerator comprising a power source and the pulse control system which is for example directly linked to the dose control system (DCM) so as to automatically stop the power source when the detected and measured absorbed dose has attained the value specified and predetermined by the operator via the man-machine interface (MMI).

Said man-machine interface (MMI) further comprises a control station (CS) and a viewing interface management program. The man-machine interface also comprises push buttons and indicator lights equipping bays, casings and/or electronic cards which contain the electronics of the control and actuation system (CAS) and the dose control means (DCM).

Advantageously, when the device is operated, a signal is produced by the detector in electric current form, said signal is measured and integrated by an electrometer during the emission of the radiation, the integrated value of said electrical signal is directly compared to the value of the dose specified and predetermined by the operator via the man-machine interface (MMI) such that, as soon as the integrated value is greater than or equal to the specified and predetermined value, the pulse signal of the grid automatically drops back to a predetermined value corresponding to the polarization voltage relative to the cathode to prevent and instantaneously stop the emission of the radiation and, possibly the high voltage source in a sufficiently short time, for example of at least 1 ns.

FIG. 4 is an embodiment representing a means for emitting ionizing radiation (MER). This means for emitting ionizing radiation (MER) comprises at least one particle source, in particular of electrons. Said source comprises for example at least one cathode (1), an anode (3) and a grid (2). The grid further comprises low voltage polarization (6) which controls the extraction and the rate of particles extracted from the cathode.

The means for emitting ionizing radiation (MER) further comprises a filament (7), supplied with voltage, in particular low voltage, to heat the cathode and thus make it emissive, that is to say so as to be able to extract particles therefrom.

The grid is configured in order for the particles extracted from the cathode to pass through the grid. The cathode and the anode are connected to a high voltage supply HT (5). Thus, the particles having passed through the grid are accelerated towards the anode while forming a beam of particles.

The particle beam source may for example be a source that can be triggered by a laser beam, or a source that can be triggered by a polarized grid or by a polarized electrode. In this first case, the source is composed of a photocathode or a plasma, an anode and a laser beam which illuminates the photocathode or the plasma to trigger the emission of electrons by the photocathode or by the plasma. The anode is provided with an aperture enabling the extraction of the particle beam and its injection into an acceleration means (8) of the particle beam (4).

The means for emitting ionizing radiation (MER) further comprises a vacuum chamber, that is to say at very pressure, for example at most $10^{-6}$ mbar.

The means for emitting ionizing radiation (MER) further comprises a transmission window or a conversion target (9) which converts the particle beam (4) into ionizing radiation (4 bis) by transmission from the vacuum chamber to the outside atmosphere. It is in this way that the ionizing radiation is emitted.

In general terms, the general principle of emission of particles or ionizing radiation is widely known in the state of the art.

The means for emitting ionizing radiation (MER) is provided with a power pulse control system which comprises a power generator supplying the means for accelerating the particle beam and switching electronics. Said power pulse control system is capable of producing a beam of energy particles that is adjustable and desired in a range comprised between 1 MeV and 50 MeV, pulsed at a desired frequency (f), typically between 5 Hz and 1 kHz, with an adjustable pulse duration (d) of at least 1 ns, preferably 0.1 µs, and capable of delivering an absorbed dose rate of up to 250 Gy/s or even of up to 500 Gy/s or even up to 1000 Gy/s.

At an adjusted and desired energy, the particle rate, in other words the current of the particle beam, is controlled by the polarization potential (6) applied to the grid. It is the combination of the energy and of the current of the particle beam which determine the absorbed dose rate which the means for emitting ionizing radiation (MER) can deliver.

The means for emitting ionizing radiation is furthermore provided with a particle beam source triggered by the grid (2). The current of the particle beam generated by the source with a grid is a direct function of the polarization potential (6) of said grid (2), in particular in the form of a signal having a pulse duration (d) of at least 1 ns, preferably 0.1 µs, a pulse frequency (f) and a polarization potential amplitude.

The switching electronics supplying said grid may operate in several modes, in particular in recurrent mode for long-duration irradiation, in mono-pulse mode for irradiation of very short duration less than preferably 1 ms, or even 100 µs, and in semi-recurrent mode for irradiations composed of several pulse trains, of frequencies chosen and separated according to the chosen periods.

Ideally, the form of the polarization signal of the grid may be programmed at will with pulses of variable duration, at variable frequency, of variable amplitude and with at least one predefined period between pulses and/or between pulse trains.

The switching electronics of the pulse power control system of the means for emitting radiation (MER) comprises analog inputs and outputs making it possible to acquire all the useful information, the configured values as well as the measured values, relative to the current and to the voltage for heating the particle beam source, and to the pulse amplitude of polarization potential of the grid.

The ionizing radiation emitter is a particle accelerator, in particular linear, for example a linear electron accelerator. The electron beam from the accelerator may be directly used as ionizing radiation after having passed through a window (9) which separates the vacuum of the accelerator chamber and the outside atmosphere, or the accelerator may be equipped with a target for converting the power of the electron beam into X-rays which then constitute the useful ionizing radiation.

The accelerator produces a particle beam of desired energy and current, in particular energy in a range comprised between 1 MeV and 50 MeV, preferably the range from 3 MeV to 25 MeV. The current and the energy are defined by the operator via the man-machine interface to obtain the desired ionizing radiation in a range chosen previously.

Advantageously, the acceleration means (8) is either a microwave frequency acceleration means or is induction or electrostatic based.

According to other features of the invention, the acceleration means (8) is particularly an accelerator cavity.

Advantageously, the means for emitting radiation (MER) further comprises several acceleration means, in particular one or more accelerator cavities, mounted in series and/or interleaved with means for deviation or recirculation of the particle beam through the one or more said acceleration means, each acceleration means being supplied by at least one power source which may be supplied by at least one modulator, said modulator itself being supplied by a high voltage source HV.

In the case of a progressive or stationary microwave frequency wave-based linear accelerator, for example in band S at 3 Gigahertz (GHz), an adjustable energy beam of electrons in a range comprised between 1 MeV and 50 MeV and of average current 100 µA may be used as ionizing radiation. Any other type of accelerator with higher and lower frequency, or even DC, that is to say electrostatic (that is to say an accelerator with DC voltage) may be used so long as the range of energy and the average current match the values indicated earlier. For example, the beam is pulsed at an adjustable frequency (f) comprised between 5 Hz and 200 Hz with a pulse a duration (d) adjustable between 0.05 µs and 4.5 µs and minimum amplitude of 100 mA.

For X-rays, it is necessary for the accelerator to be powerful, capable of accelerating a primary beam of electrons of average intensity greater than 1 mA. This accelerator may be a linear accelerator with a copper cavity or a superconducting linear accelerator, or any other type of accelerator corresponding to the requirements of the expected result of the present invention.

In the case of a linear accelerator comprising a copper cavity, it is pulsed at frequencies (f) greater than 200 Hz, with a pulse a duration (d) of at least 5 µs and a peak intensity of at least 1 A. It may be constituted by several accelerator cavities in series, each supplied by its own high frequency (HF) power source. The power sources may be amplification means comprising a vacuum chamber and making it possible to perform amplifications of medium and high power with a narrow microwave frequency band, for example klystrons, and these amplification means are themselves supplied by conventional or solid state modulators.

To provide a pulsed beam at an adjustable frequency (f), an adjustable pulse duration (d) and an adjustable peak current amplitude, the beam source of the accelerator comprises a DC or electrostatic electron gun (that is to say an electron gun using DC voltage) of triode type or photocathode type triggered by laser or of plasma type triggered by electrode or by laser. It may for example be a high voltage DC gun with a thermo-ionic cathode with a grid. The cathode is brought to a negative potential of around ten kilovolts to several tens of kilovolts. The anode remains at ground potential, in particular 0 V (zero volt). The grid then plays the role of trigger by being brought to a negative potential less than around ten volts or around a hundred volts relative to the cathode so as to not to emit and to a negative potential but greater than that of the cathode to emit. The amplitude of the peak current emitted by the cathode depends on its potential difference relative to that of the grid. Pulses with adjustable frequency (f), adjustable duration (d) and with adjustable voltage amplitude are sent to the grid in phase with the high voltage (HV) pulses of supply for the cathode to generate a desired pulsed beam which is injected for the acceleration of the particles in the high frequency (HF) cavities of the accelerator.

The device according to the invention has the advantage of giving the operator the possibility of programming the type of ionizing radiation, the radiation energy, the dose rate of ionizing radiation absorbed and/or to deliver, and the duration of the irradiation or the dose of ionizing radiation to be absorbed and/or to deliver.

It enables controlled and accurate delivery in desired manner via the man-machine interface, intelligently, of high doses of ionizing radiation of at least 0.01 Gy, or even 0.25 Gy with an accuracy of at least 1 µGy, preferably 1 nGy, in energies in a range comprised between 1 MeV and 50 MeV, in very short times, typically comprised between 0.1 µs and 100 ms, preferably 100 µs or even 1 ms.

It also enables, for other applications, controlled and accurate delivery, in desired manner, via the man-machine interface, of high dose rates of ionizing radiation up to 250 Gy/s, at energies in ranges comprised between 1 MeV and 50 MeV, in very short times of at least 50 ns, for radiotherapy and/or radiobiology purposes.

It can thus be seen that it is possible to industrially produce a radiotherapy and/or radiobiology machine capable of delivering a high accurate and specified dose of ionizing radiation, for example 10 Gy, in very short times, for example 100 ms.

Contrary to the prejudices which were to believe that it is impossible to design a radiotherapy machine capable of giving the above-described performances, the invention presented here enables it to be shown that by using the machine described in this invention, it is possible to solve the previously cited problem.

The present invention is not at all limited to the embodiments described and represented, but the person skilled in the art will know how to make any variant thereof conforming to its spirit.

The invention claimed is:

1. An irradiation device using ionizing radiation, including for radiotherapy and/or radiobiology, simultaneously comprising at least:
   a means for emitting ionizing radiation (MER) comprising:
      at least one particle source which comprises at least:
         a cathode and an anode, or a plasma,
         a means for triggering particle emission, and
         a means for accelerating a particle beam, and
      a system for power pulse control,
   an ionizing radiation dose detection means (DDM) comprising a detector,
   a dose control means (DCM), configured to control triggering and stopping of the means for emitting ionizing radiation (MER), comprising:
      control electronics (CE),
      an amplifier and/or an attenuator amplifying and/or attenuating a signal emitted by the detector,
      an integrator integrating, during a time of particle emission, said amplified and/or attenuated signal into an integrated signal, and
      a comparator continuously comparing said integrated signal to settings for a specified dose (SAD) predetermined by an operator,
   a control and actuating system (CAS) comprising:

a system for functional control (SFC) of members of said irradiation device, comprising:
a man-machine interface (MMI),
viewing tools, and
implementation means configured in order for the operator to program, at a single time, a nature of the radiation, an absorbed dose rate of ionizing radiation, a duration for the emission of the ionizing radiation, and the pulse settings,
wherein said means for emitting ionizing radiation (MER), said ionizing radiation dose detection means (DDM), said dose control means (DCM) and said control and actuating system (CAS), are configured for delivering and controlling doses of ionizing radiation of at least 0.01 Gy with an accuracy of at least 1 µGy at energies comprised between 1 MeV and 50 MeV, for times comprised between 0.1 µs and 100 ms,
wherein the system for power pulse control of the means for emitting ionizing radiation (MER) is configured for producing a particle beam of ionizing radiation, of energy in a range comprised between 1 MeV and 50 MeV, pulsed at a frequency (f) comprised between 5 Hz and 1000 Hz, with a pulse duration (d) of at least 1 ns, and for delivering an absorbed dose rate of at least 0.01 Gy/s,
wherein the control electronics (CE) of the dose control means (DCM) is configured for controlling a dose delivered for at least 0.1 µs, and
wherein the detector is an ultra-fast detector, coupled to a dose control means (DCM), configured to detect a dose of ionizing radiation in at least 0.01 ns and at dose rates of at least 0.01 Gy/s.

2. The irradiation device using ionizing radiation according to claim 1, wherein the means for emitting ionizing radiation (MER) is a particle accelerator comprising a power source and a pulse control system, said pulse control system being directly linked to the dose control means (DCM) so as to automatically stop the power source when the absorbed dose, detected and measured, has attained a value specified and predetermined by the operator via the man-machine interface (MMI), said man machine interface (MMI) further comprises a command station (CS) and a viewing interface management program.

3. The irradiation device using ionizing radiation according to claim 1, wherein the means for accelerating a particle beam is a microwave frequency acceleration means.

4. The irradiation device using ionizing radiation according to claim 1, wherein the means for emitting radiation (MER) further comprises plural of said means for accelerating a particle beam mounted in series and/or interleaved with means for deviation or recirculation of the particle beam through the plural means for accelerating a particle beam, each being supplied by at least one power source.

5. The irradiation device using ionizing radiation according to claim 1, wherein the detector is a semiconductor, diamond in monocrystalline or polycrystalline form, pure or doped, comprised between two polarization electrodes at terminals of which is applied a potential of plural volts adjustable according to a thickness of the detector via the man-machine interface, and is configured to obtain a response time of at least 0.01 ns, at high dose rates of at least 0.01 Gy/s.

6. The irradiation device using ionizing radiation according to claim 1, wherein the control electronics (CE) of the dose control means (DCM) comprises means for measuring electric current, of an electrical signal, produced by the interaction of the ionizing radiation with the detector, means for converting said electric current into absorbed dose rate units and means for integrating said electric current that are configured to accurately measure the absorbed dose accumulated during the emission of the ionizing radiation.

7. The irradiation device using ionizing radiation according to claim 1, wherein an electrical signal is produced by the detector, said electrical signal is measured and integrated by an electrometer during the emission of the ionizing radiation, the integrated value of said electrical signal is directly compared to the value of the dose specified and predetermined by the operator via the man-machine interface such that, as soon as the integrated value is greater than or equal to the specified and predetermined value, the signal of the means for triggering particle emission is interrupted to instantaneously stop the emission of the ionizing radiation, and preferably the high voltage source, in at least 1 ns.

8. The irradiation device using ionizing radiation according to claim 1, wherein the detector comprises at least one of the group consisting of quadrants, sectors, and voxels, each producing a detection signal (ADS) and configured to enable information to be deduced, from the detection signals (ADS), characterizing a position, a shape, and an energy of the ionizing radiation beam which passes through them, and furthermore so as to control and regulate the ionizing radiation beam, including the position, the shape and the energy of the ionizing radiation beam.

9. The irradiation device using ionizing radiation according to claim 1, wherein the detector comprises at least one of the group consisting of quadrants, sectors, and voxels, each producing a detection signal (ADS) and configured to enable information to be deduced, from the detection signals (ADS), characterizing at least one of the group consisting of a position, a shape, and an energy of the ionizing radiation beam which passes through them, and furthermore so as to control and regulate the ionizing radiation beam, including the at least one of the group consisting of the position, the shape and the energy of the ionizing radiation beam.

10. The irradiation device using ionizing radiation according to claim 1, wherein the means for triggering particle emission includes a grid, an electrode, or a laser.

11. The irradiation device using ionizing radiation according to claim 1, wherein the means for accelerating a particle beam is induction based.

12. The irradiation device using ionizing radiation according to claim 1, wherein the means for accelerating a particle beam is electrostatic based.

13. The irradiation device using ionizing radiation according to claim 1, wherein the detector is a semiconductor, comprised between two polarization electrodes at terminals of which is applied a voltage potential adjustable according to a thickness of the detector via the man-machine interface, and is configured to obtain a response time of at least 0.01 ns, at high dose rates of at least 0.01 Gy/s.

14. The irradiation device using ionizing radiation according to claim 1, wherein the means for emitting radiation (MER) further comprises plural of said means for accelerating a particle beam and means for deviation or recirculation of the particle beam through the plural means for accelerating a particle beam.

* * * * *